United States Patent [19]

Neihof

[11] Patent Number: 5,858,307

[45] Date of Patent: Jan. 12, 1999

[54] HYDROGEN SULFIDE ANALYZER WITH PROTECTIVE BARRIER

[75] Inventor: Rex A. Neihof, Ft. Washington, Md.

[73] Assignee: The United States of America as represented by the Secretary of the Navy, Washington, D.C.

[21] Appl. No.: 575,415

[22] Filed: Dec. 20, 1995

Related U.S. Application Data

[62] Division of Ser. No. 321,182, Sep. 29, 1994, Pat. No. 5,529,841.

[51] Int. Cl.$^6$ ....................................................... G01N 31/22
[52] U.S. Cl. ............................ 422/61; 436/120; 436/121; 436/808; 116/206; 215/230
[58] Field of Search ........................................ 428/447, 328, 428/332, 339, 452; 116/200, 206; 95/49, 8, 55; 215/230; 55/214; 436/120, 121, 122, 808; 422/61; 23/293 S

[56] References Cited

U.S. PATENT DOCUMENTS

| | | | |
|---|---|---|---|
| 4,174,202 | 11/1979 | Simpson | 436/121 |
| 4,348,358 | 9/1982 | McKee et al. | 422/56 |
| 4,772,560 | 9/1988 | Attar | 436/165 |
| 5,364,593 | 11/1994 | Mihaylov et al. | 422/87 |

*Primary Examiner*—Stevan A. Resan
*Assistant Examiner*—D. Lawrence Tarazano
*Attorney, Agent, or Firm*—Thomas E. McDonnell; George Kap

[57] ABSTRACT

A field test kit for determining quantity of hydrogen sulfide in a liquid test sample. The test kit includes a test container with an opening for a liquid test sample containing hydrogen sulfide gas and a cap provided over the opening. The cap has calorimetric particulate indicator on its top inside surface. A silicone barrier disposed over the indicator protects the indicator from contact with the test sample.

11 Claims, 2 Drawing Sheets

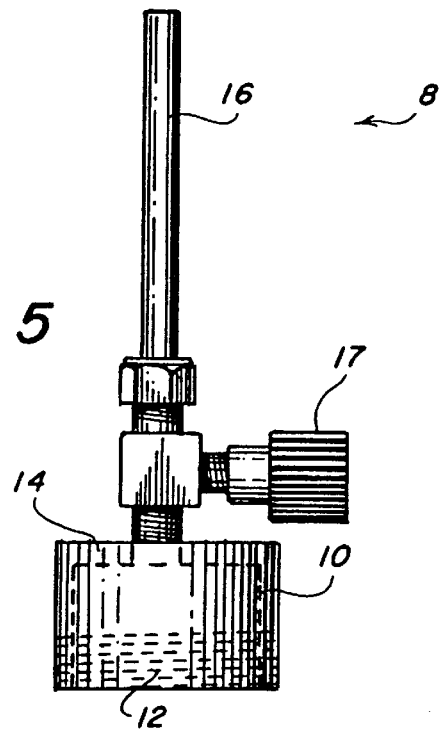
FIG. 5
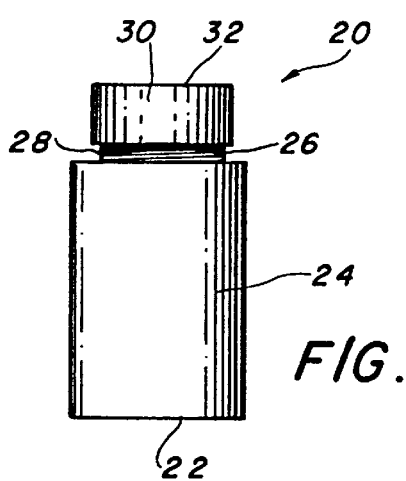
FIG. 1
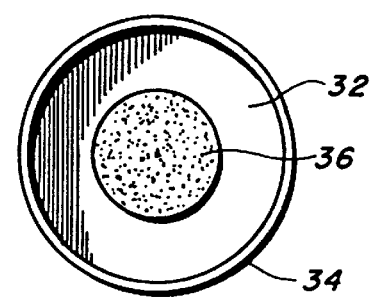
FIG. 2
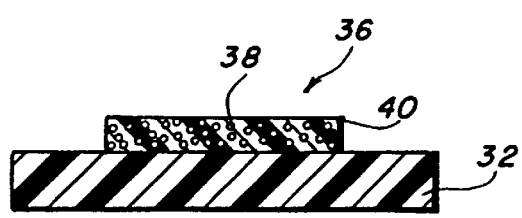
FIG. 3
FIG.6(a)   FIG.6(c)   FIG.6(e)
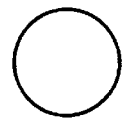 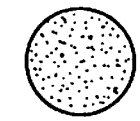 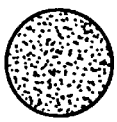 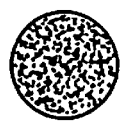
ppm 1   ppm 5   ppm 8   ppm 12   ppm 20
FIG.6(b)   FIG.(d)

HYDROGEN SULFIDE ANALYZER WITH PROTECTIVE BARRIER

This application is a division of application Ser. No. 08/321,182, filed Sep. 29, 1994 now U.S. Pat. No. 5,529,841.

FIELD OF INVENTION

This invention pertains to the field of gas analyzers, and more particularly, to hydrogen sulfide calorimetric analyzers.

BACKGROUND OF INVENTION

Hydrogen sulfide ($H_2S$) is a toxic gas that is detectable by humans as a rotten egg odor at a concentration in air of 0.001 ppm or less. A human begins to lose ability to smell hydrogen sulfide at about 100 ppm thereof. Hydrogen sulfide becomes very toxic at about 800–1000 ppm accompanied sometimes with a brief sickeningly sweet smell. Human death occurs in 30 minutes when exposed to a concentration of 1000 ppm of hydrogen sulfide. The threshold limit value (TLV) imposed by OSHA for human exposure to hydrogen sulfide is 10 ppm for 8 hours, not to exceed 15 ppm for more than 15 minutes.

Serious hydrogen sulfide toxicity problems have arisen on ships employing a foaming agent mixed with water in fire fighting systems. Sulfate in seawater is chemically reduced by anaerobic bacteria present in the seawater to produce hydrogen sulfide in toxic amounts. Seawater contains about 800 ppm sulfur as sulfate. If all of the sulfate in seawater were converted to dissolved hydrogen sulfide, the concentration would be about 850 ppm, an amount which can be highly toxic to humans if released as a gas in air in a confined space.

The rate at which sulfate-reducing bacteria generate hydrogen sulfide from sulfate-containing waters depends on the activity of the bacteria which remove oxygen, on nutrients, temperature and other conditions. It may take several weeks or months to produce a dangerously high concentration of hydrogen sulfide in a fire fighting system. At that time, the system is normally flushed out and refilled with fresh foaming agent and seawater. This operation is expensive and may be damaging to the marine environment.

In crude oil, hydrogen sulfide is present in widely varying concentrations from zero to several hundred ppm, depending on the source of the crude oil. A knowledge of the concentration of hydrogen sulfide in crude oil, or in any commercially used liquid containing hydrogen sulfide, is desirable in dealing with possible problems of human toxicity arising during transportation and storage, environmental pollution, or subsequent refining operations.

Laboratory analysis procedures are available for determining hydrogen sulfide in liquids and gases and calorimetric test kits are on the market in the form of detector tubes and papers, badges and electronic instruments to test for hydrogen sulfide in the field. However, field test kits employing calorimetric indicators are rendered inoperable by samples producing foam on aeration which wets the indicator or by samples which are colored by dissolved, particulate or soluble matter. Field test kits for direct determination of hydrogen sulfide in crude oil and in fire-fighting foams are not available.

OBJECTS OF INVENTION

It is an object of this invention to provide for a dependable and repeatable determination of hydrogen sulfide concentrations in liquids on the basis of visual observation of an indicator material which changes color in the presence of hydrogen sulfide.

It is another object of this invention to provide a protective barrier, over or surrounding the calorimetric indicator material, that is permeable to hydrogen sulfide and impermeable to the liquid test sample.

It is another object of this invention to provide a silicone polymer barrier between the test sample and calorimetric indicator wherein the silicone barrier is insoluble and/or not swellable when it comes in contact with the test sample.

It is another object of this invention to provide a field test kit to determine the concentration of dissolved hydrogen sulfide in a liquid test sample through the use of a silicone polymer-protected indicator which undergoes a visible change in color intensity directly proportional to the concentration of hydrogen sulfide dissolved in the liquid sample.

These and other objects of this invention are attained by having particles of a calorimetric indicator embedded in a silicone polymer barrier or by providing a continuous silicone film between a calorimetric indicator and a test sample containing hydrogen sulfide, which silicone barrier and film are not soluble and/or not substantially swellable when in contact with the test sample.

BRIEF DESCRIPTION OF DRAWINGS

FIG. 1 is an elevation view of a test container with a cap screwed thereon. The container is used to hold a liquid test sample to be analyzed for the presence of hydrogen sulfide.

FIG. 2 shows an interior view of container cap closure attached to the inner surface thereof a layer of silicone polymer barrier in which a calorimetric hydrogen sulfide indicator is embedded.

FIG. 3 is a cross-sectional view showing the disposition of the silicone barrier with embedded indicator on a substrate.

FIG. 5 is an illustration of a typical sampler tube that is used to extract a sample of a fire-fighting foam.

FIG. 6 is an illustration of a typical standard for determining the concentration of dissolved hydrogen sulfide in a liquid test sample where the numbers are in ppm of hydrogen sulfide wherein FIG. 6(*a*) represents 1 ppm, FIG. 6(*b*) represents 5 ppm, FIG. 6(*c*) represents 8 ppm, FIG. 6(*d*) represents 12 ppm, and FIG. 6(*e*) represents 20 ppm.

DETAILED DESCRIPTION OF INVENTION

Figure 4:
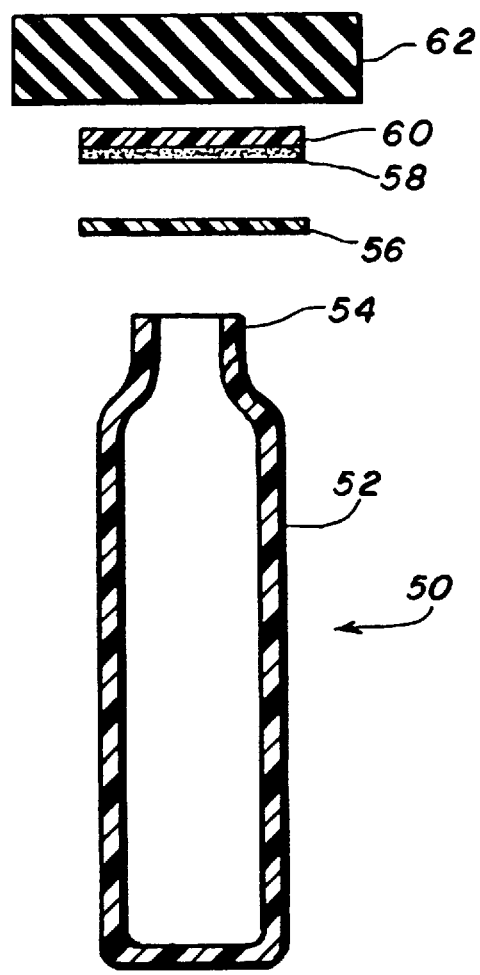
FIG. 4 is another embodiment of this invention in which the indicator is disposed on a separate substrate and is pressed in contact with a film of silicone polymer barrier which in turn is pressed against the neck opening of the sample container.

The present invention provides a protective silicone barrier between the calorimetric indicator on the inside surface of a cap and container holding the test sample solution. This invention will be described in connection with a hydrogen sulfide analysis kit consisting of a test container to hold a liquid test sample. The neck of the container can accept a cap holding the calorimetric indicator and the protective barrier secured to the inside of the cap so that any hydrogen sulfide emanating from the liquid test sample disposed in the test container would come in contact with the indicator on the cap.

The sample container may be of any desired shape or size so long as it is adapted to being closed in such a way as to allow exposure of the liquid sample to a silicone barrier which protects hydrogen sulfide indicator from the liquid sample. A conventional glass or plastic bottle or vial constitutes a convenient sample container. For convenience, the container should be transparent or translucent and graduated or otherwise inscribed with a mark designating a known volume so that the volume of sample used can be easily observed. Containers must be resistant to deterioration by the liquid being sampled.

A suitable cap for the bottle container is conventionally made of plastic, glass or metal. The cap has screw threads corresponding to the threads on the neck of the container. In one embodiment of the invention, the cap is provided with a liner which carries the silicone/indicator and also prevents leakage of sample when the container is closed.

In an alternative arrangement useful especially for the simultaneous analysis of a number of smaller samples, glass vials are used with smooth-edged openings at the top over which is pressed a plastic sheet supporting the silicone/indicator film. In this version, the barrier and the supporting sheet close the vial, and thus prevent leakage of the liquid sample. A good seal is assured by pressing the sheet against the lip of the vial opening with a soft rubber pad. Sealing is conveniently done in a rack for holding multiple vials and provided with a clamping arrangement to exert pressure on the rubber pad.

The calorimetric indicators useful herein are in finely divided form, typically having a maximum particle size below 100 microns. More uniform colorations are obtained with indicators of smaller particle sizes. Suitable herein are calorimetric indicators selected from lead acetate, copper sulfate, silver nitrate, copper thiocyanate and others that change color when contacted by hydrogen sulfide gas. Lead acetate is a very sensitive indicator while copper sulfate and copper thiocyanate are less sensitive but still useful in some applications. Different indicators will present different color changes and different sensitivities when contacted with hydrogen sulfide. For use with a continuous barrier, as defined herein, these salts may be dissolved in water typically to about 5–10% concentration, and spread on a wettable plastic sheet and allowed to dry. Alternatively, a solution of the salts may be used to saturate a filter paper support, followed by drying in air. For use in a discontinuous barrier, as defined herein, the indicator is powdered sufficiently to pass a screen with openings of less than 50 microns. The concentration of indicator in the precured silicone polymer material is about 1–20%, based on the weight of the silicone and the indicator, and typically about 2–5% for lead acetate and 10–20% for the copper salts.

The protective barrier between the test sample and the calorimetric indicator is a cured silicone polymer in solid form. Silicone polymers are thermally and oxidatively stabile and have only a relatively mild dependance of physical properties on temperature. Other important characteristics of the silicone barriers include a high degree of chemical inertness, resistance to weathering, good dielectric strength, and low surface tension.

Silicone polymer barriers are one to several orders of magnitude more permeable to gases than organic polymers and yet are impermeable to water, oil and other liquids. Diffusion rates of hydrogen sulfide through silicone films is of the same order as for other highly permeable gases such as oxygen and carbon dioxide. Therefore, the unusually high permeabilities through silicone barriers are mainly due to the high rate of diffusion of the dissolved hydrogen sulfide in the test sample. This property of silicone barriers is a direct result of the greater flexibility or mobility of the Si—O bond as compared to the C—C or the C=C bond characteristic of the polymeric backbone of natural rubber.

A silicone polymer is characterized by the repeating siloxane group, i.e., Si—O—Si. A silicon atom usually has four bonds, one of which can be used to cross-link with other siloxane chains during drying when curing takes place and two of which can be attached to various groups which include lower alkyl, phenyl, fluoro, nitrile and others. For lower alkyl substituents of about 1 to 6 carbon atoms, the bulkier the groups attached to the silicon atom, the lower permeability of the silicone films made from such siloxanes.

A silicone polymer contains a repeating silicon-oxygen or siloxane backbone and has organic groups attached to a significant proportion of the silicon atoms by means of the silicon-carbon bonds. In commercial silicones, the organic groups are typically methyl, ethyl, fluoroalkyl, phenyl, vinyl, and other groups which are provided for specific purposes. Some of the groups in the polymer can also be hydrogen, chlorine, fluorine, nitrile, alkoxy, acyloxy, alkylamino, etc.

Polydimethyl silicone film has the highest permeability to hydrogen sulfide compared to other dialkyl silicone films. Substitution of any one or more of the methyl groups by bulkier alkyl or phenyl groups will result in reduced permeability. Fluorosilicone film has substantially lower permeability than dimethyl silicone film and nitrile silicone film has even lower permeability than flurosilicone film.

Polydimethyl silicone films are highly permeable to hydrogen sulfide and are suitable for use as barriers when determining hydrogen sulfide in aqueous test samples. However, polydimethyl silicone films tend to swell in the presence of hydrocarbons, especially aromatic hydrocarbons such as oils. Swelling of polydimethyl silicone films in the context of this invention is undesirable. Swelling of a silicone film changes the permeability to hydrogen sulfide and, therefore, changes the sensitivity of the test. Fluorosilicone barriers are much more resistant to swelling in oils. Although the permeability of fluorosilicone barriers to hydrogen sulfide is less than with polydimethyl silicone barriers, their sensitivity is sufficient for determining hydrogen sulfide in oils. Control over permeability of barriers to hydrogen sulfide can be obtained by using a mixture of polydimethyl silicone and fluorosilicone polymers in liquid solution for casting the barriers. Depending on the liquid being analyzed, such mixed polymer barriers can give adequate sensitivity and still not swell significantly. Typical mixtures can be made in weight ratio of about 0.1–5, more typically 0.5–2, of polydimethyl or any other lower alkyl silicone to fluorosilicone.

The protective barrier can conveniently be made from commercially available liquid silicone polymer materials which are spread in a thin film on a substrate. A final curing or crosslinking process is necessary to insolubilize and stabilize these materials. Those materials which are most convenient in the present context incorporate a crosslinking agent consisting of a hydrolyzable polyfunctional silane or siloxane which, on activation by atmospheric moisture in the presence of a catalyst, can react with the linear silicone polymer chains to form a crosslinked network. Commercially, these polymers are described as room temperature vulcanized (RTV).

Suitable material is Dow Corning dispersion DC 94-003 product which is an example of a polydimethyl liquid silicone material with high permeability to hydrogen sulfide in the cured form. This product has the following given composition on weight basis:

| | |
|---|---|
| trifluoropropylmethyl siloxane | 45% |
| trimethylated silica | 6% |
| vinyl tri(methyl ethyl ketoxime)silane | 6% |
| methyl ethyl ketone | 40% |

For use in the present invention, the trimethylated silica in the DC 94-003 product is preferably removed because of the color it imparts to barriers prepared from it. This can be conveniently done by diluting one volume of the polymer with one volume of hexane and centrifuging for one hour at about 12,000 rpm. The colored particulate matter is sedimented and the clear supernatant solution is used in preparing the barriers.

The Dow Corning RTV Coating 3140 has the following weight percentage composition:

| | |
|---|---|
| methyl trimethoxy silane | 6% |
| trimethylated silica | 16% |
| polydimethyl siloxane | 78% |

Dow Corning 203 siloxane liquid polymer has the following given composition on weight basis:

| | |
|---|---|
| polydimethyl siloxane | 35% |
| petroleum light aliphatic hydrocarbons | 30% |
| titanium dioxide | 30% |
| aluminum oxide | 1% |
| amorphous silica | 2% |
| vinyl trimethylene ketoxime silane | 2% |

The protective barrier can be a discontinuous silicone polymer barrier enveloping dispersed powder particles of the indicator or a continuous silicone film situated between a deposited layer of indicator particles and the test sample and preventing contact between the indicator and the liquid test sample. The thickness of the discontinuous barrier and the continuous silicone film contemplated herein is typically in the range of 10–1000 microns, more typically 20–200 microns. The thickness of the silicone polymer barriers can be controlled during preparation by varying the concentration of polymer in the liquid used for casting the barrier and by varying the depth of the liquid layer and the area of substrate over which it is spread for drying and curing. In general, the barrier should be sufficiently thin for rapid gas transmission, but thick enough to avoid pin holes which might be penetrated by the sample liquids.

The terms "discontinuous" and "continuous" silicone barriers used herein are only meant to distinguish one form of barrier from another. In a discontinuous silicone barrier, the silicone polymer coats individual indicator particles. Essentially all of these indicator particles are individually coated. The discontinuous barrier thus acts as a protective barrier between the indicator particles and the test sample. A continuous silicone barrier is generally a planar film or membrane disposed over the mass of indicator particles as a sheet which is adjacent to and preferably in contact with the indicator particles. The continuous film does not envelop the individual indicator particles, and thus acts as a continuous barrier between the indicator particles and the test sample.

An indicator with a discontinuous silicone barrier can be prepared by mixing the indicator in particulate or powder form with a silicone polymer in a liquid hydrocarbon, such as hexane or xylene, and applying the dispersion in a thin layer on the interior surface of the sample container cap. After about 24 hours in a normal room atmosphere, the hydrocarbon evaporates and the silicone polymer cures with the indicator particles embedded in a solid protective film.

A number of variations can be used to provide a discontinuous silicone barrier on the indicator particles. The indicator can be dispersed in a hydrocarbon liquid and then the silicone solution added and stirred to obtain a uniform suspension of indicator particles. Alternatively, the required amount of an indicator can be dissolved in a small amount of an alcohol and then a hydrocarbon solution of the silicone polymer added and thoroughly mixed to precipitate and disperse the indicator in a finely divided state. Subsequent procedures for preparing solid silicone barriers from dispersions of indicators made by either method are the same.

The silicone polymer containing the dispersed calorimetric indicator is then deposited on cap or a substrate in a thin layer and dried to remove the hydrocarbon solvents or dispersants. The drying step can be carried out at normal room tamperature or at an elevated temperature. A curing or cross-linking process is allowed to take place to insolubilize and stabilize the silicone polymer. Cross-linking is conveniently carried out with silicone polymers which can be activated by the water vapor content of normal room air. With thin barriers of less than about 500 microns, an exposure for about 24 hours at a relative humidity of at least 20% is typically sufficient for activation. The result is a stabilized discontinuous silicone barrier in the sense that it contains dispersed and embedded indicator particles. The particles respond when contacted by hydrogen sulfide vapor but are protected from dissolution or removal by the liquid test sample.

A continuous silicone barrier in the form of a film or membrane can be provided as a protective barrier between the indicator disposed on the inside of the cap or a substrate and the test sample disposed in the test container. Such a barrier can be formed in situ over the indicator by providing a layer of a liquid silicone material thereover and drying, and then curing to obtain a dried silicone film over the indicator. Also, the silicone film can be made elsewhere and applied over the indicator to function as a protective barrier. The barrier has sufficient adhesion to adhere to the substrate.

The viscosity of the silicone solutions or dispersions can be reduced by the addition of hydrocarbon liquid thereto so that a thin and uniform barrier can be obtained. Hydrocarbon liquid can be used to dilute the silicone dispersion to about 10–60% w/v so that a free flowing liquid is obtained. A suitable concentration of an indicator in the silicone dispersion is about 1–20%, and more typically 2–5% w/v, but this amount can be varied depending on the sensitivity desired.

Various liquid test samples can be analyzed for hydrogen sulfide using the components of the test kit described above. Liquid test samples suitable for analysis range from crude, refined or residual oils to aqueous emulsions and solutions. An example is the aqueous foaming agent/seawater solution used for fighting fires on ships and elsewhere. Well known products that may be tested according to the present invention contain surfactants, metal deactivators, and refractive index adjusters, with the remainder being water and other optional ingredients.

As used on certain ships, the foaming agent concentrate is mixed with seawater and stored in pipes comprising the fire fighting system. In time, this solution can become stagnant due to the action of aerobic and anaerobic bacteria which can flourish on the nutrients in the seawater. Thus, hazardous concentrations of hydrogen sulfide can be generated. It is an objest of the kit described here to detect the presence of such concentrations of hydrogen sulfide so that precautionary measures can be taken.

The concentration of hydrogen sulfide in crude oil varies widely from negligible to several hundred ppm. Since the amount of hydrogen sulfide in a crude oil test sample is not definitely known, it is an object of the test kit described above to determine presence and amount of hydrogen sulfide so that precautions can be taken during transportation, storage, and refining thereof.

A test sample with a high concentration of hydrogen sulfide can be brought within the range of the test by dilution of a known amount of the test sample with hydrogen sulfide-free liquid. Alternatively, the sensitivity of the kit can be decreased if desired and the range of hydrogen sulfide concentrations to which the kit shows a variable response moved in the direction of higher hydrogen sulfide concentrations by changing kit parameters to increase the thickness of the silicone barrier and/or to decrease the exposure time of the barrier/indicator to the sample liquid.

It is believed that a concentration of as low as about 0.5 ppm hydrogen sulfide in the test sample can be detected using the field test disclosed herein. Increments of 0.5 ppm can be resolved in the 1–3 ppm range, increasing to increments of 2 ppm in the 8–16 ppm range.

BRIEF DESCRIPTION OF THE FIGURES

FIG. 1 illustrates a test container.

FIG. 2 illustrates a cap for the test container having an indicator layer.

FIG. 3 illustrates a cross-sectional view of the indicator laminate of the invention.

FIG. 4 illustrates a cross-sectional view of a test container and cap.

FIG. 5 illustrates a sampler for extracting sample material.

FIG. 6 illustrates the reactivity of the invention to hydrogen sulfide to form a standard for comparison.

The components used to obtain a test sample-and to determine hydrogen sulfide therein include the test container with the cap of FIG. 1 and the cap of FIG. 2. FIG. 3 is a partial cross-section of FIG. 2 which illustrates the indicator and the discontinuous silicone barrier around the indicator particles on a substrate.

The test container 20 of FIG. 1 is a typical bottle-type receptacle which can be circular, rectangular, or of any other shape in cross-section. The test container can be made of any material desired, typically translucent glass or plastic, for visibility, as the test solution is introduced thereinto. The test container includes bottom wall 22, side wall 24 and neck 26. The neck is of a reduced size relative to the width of the container width and typically has screw threads 28 on its external surface.

The cap shown in FIG. 2 in greater detail includes planar circular member top wall 32 and a flange or a skirt 34 extending downwardly at about 90° to the circular member. The cap can have a threaded portion (not shown) on the inner surface of flange 34 which threaded portion mates with screw threads 28 on neck 26 of test container 20 when the cap is screwed onto the neck of the test container. The indicator and the silicone barrier 36 are attached to the inside of the cap to circular member 32, are shown in greater detail in FIG. 3 which is a partial cross-section through the cap.

In FIG. 3, reference numeral 36 generally refers to the indicator particles and the discontinuous silicone barrier in solid, cured state enveloping the indicator particles. In FIG. 3, circular member or substrate 32 has secured thereto indicator particles 38 dispersed in discontinuous silicone barrier 40.

FIG. 4 illustrates another embodiment of this invention. In this embodiment, test sample container 50 with side wall 52 and neck 54 has continuous silicone barrier film 56 disposed directly thereover. Indicator 58 and substrate 60 are disposed over barrier film 56 and pad 62 is disposed thereover. The indicator is shown as a continuous powdery layer attached to substrate 60 by adhering thereto. The substrate, however, can be impregnated with the indicator. In operating condition, with a test sample in the test sample container, the pad presses the substrate, the indicator and the barrier film against the top of the neck of the test sample container in a fluid tight fashion.

FIG. 5 illustrates a sampler for extracting a sample from a ship's fire-fighting system. Sampler 8 includes elongated tube 16 attached to nozzle 14 having inner portion 10 which fits over a pipe leading from a ship's fire-fighting system. Inner threaded portion 12 on the nozzle secures the nozzle to the pipe. Intermediate valve 17 secured to the tube is used to control flow through the tube. In operation, sampler 8 is attached to a pipe leading from a ship's fire-fighting system by attaching nozzle 14 to the pipe and allowing test sample to pass through tube 16 into a test container.

FIG. 6 illustrates a typical standard with darker colors corresponding to greater concentrations of hydrogen sulfide in the liquid sample. Such a standard is prepared using known concentrations of hydrogen sulfide in the same type of liquid for which the kit is intended. Sample container, cap and silicone barrier/indicator arrangement, sample volume and exposure time are also the same as employed in assaying unknown concentrations of hydrogen sulfide in liquid samples. The indicators with colors corresponding to a range of hydrogen sulfide concentrations are preferably recorded photographically to provide a permanent reference.

The first step in making an analysis with the kit described herein is to introduce a known volume of sample into the sample container. This should be done with minimal exposure of the sample to air in order to prevent loss of hydrogen sulfide by volatilization and reaction with atmospheric oxygen. Splashing and entrainment of air bubbles during this operation should be avoided. Immediately after placing the liquid to be analyzed into the sample container, the cap carrying either a continuous or discontinuous silicone barrier with indicator, or the closure of FIG. 4, is secured to the container. The container is inverted to bring the liquid in contact with the barrier thus minimizing the diffusion path of hydrogen sulfide from the liquid to the barrier surface.

The container is shaken or swirled gently in the inverted position for a measured period of time, usually 3–10 minutes, depending on how the adjustable variables of the test are chosen. After the exposure period, the cap or the closure is removed trom the sample container and the color of the indicator observed. If the indicator is obscured by colored or particulate matter from the sample, clearing can be accomplished by directing a gentle stream of clear liquid on the barrier. Water is satisfactory for aqueous samples and mineral spirits or other hydrocarbon liquid can be used for oils. The color of the indicator may then be compared with a set of standard reference colors obtained by running identical tests with known concentrations of hydrogen sulfide in a liquid similar to the test sample. Such reference color standards are preferably reproduced photographically for permanent reference. Interpolations between adjacent standard colors may be necessary to estimate the concentation of hydrogen sulfide in the sample.

The invention having been generally described, the following examples are given as particular embodiments of the invention to demonstrate the practice and advantages thereof. It is understood that the examples are given by way of illustration and are not intended to limit the specification or the claims that follow, in any manner.

EXAMPLE 1

This example demonstrates the determination of hydrogen sulfide in seawater containing a 6% aqueous solution of a fire fighting foam (3M product FC-206 CF, Light Water Brand Aqueous Film-Forming Foam), wherein the hydrogen sulfide determination was made with a lead acetate particulate indicator protected from the aqueous solution by a continuous silicone film.

A silicone film of about 130 microns in thickness was prepared by spreading Dow Corning 203 silicone liquid material on a smooth Teflon® surface and allowing a day for curing in room atmosphere. Silicone film squares measuring 2 cm on a side were cut from the film and subsequently stripped off the Teflon surface, as needed.

A square of filter paper measuring 2 cm on a side was impregnated with an aqueous lead acetate [$Pb(C_2H_3O_2)_2 \cdot 3H_2O$] solution and dried. The aqueous indicator solution contained 5% lead acetate and deposition of lead acetate on the filter paper was about 0.6 mg/cm$^2$.

The test container was a 25-ml glass vial containing 20 ml of the aqueous solution test sample composed of seawater and 6% of the fire-fighting foam agent. The aqueous solutions used in this experiment contained predetermined concentrations of hydrogen sulfide.

The 2-cm square of the silicone film was spread evenly over the neck of the vial, the 2-cm square of the indicator-impregnated filter paper was placed on top of the silicone film and a rubber pad was placed over the filter paper to press the silicone film and the filter paper against the neck of the vial. The vial was then inverted and was shaken for 10 minutes following which, darkening of the indicator was observed.

At 2 ppm of hydrogen sulfide in the aqueous sample solution, a barely detectable darkening of the indicator occurred. Darkening of the indicator was apparent at 4 ppm which increased to light brown at 8 ppm and to dark brown at 20 ppm.

EXAMPLE 2

This example demonstrates the determination of hydrogen sulfide in crude oil by means of lead acetate indicator dispersed in a discontinuous silicone barrier.

Pursuant to the objects of this example, 0.66 mg of powdered lead acetate indicator was dissolved with mixing in 0.3 ml of methanol and 0.3 g of Dow Corning 3140 dimethyl silicone liquid polymer followed by addition with mixing of 0.1 ml of xylene and 1 ml of diluted and clarified fluorosilicone liquid polymer Dow Corning 94-003. Dilution of the fluorosilicone polymer was with one volume of hexane. The weight ratio of the dimethyl silicone polymer Dow Corning 3140 to the fluorosilicone polymer Dow Corning 94-003 was about 1/1. A small test tube was used to carry out the mixing operations described herein and stirring was performed with a Teflon® coated stirring rod.

After thorough mixing, 0.05 ml drops of the liquid silicone/indicator material was dispensed in the center of matte-surfaced Mylar® plastic bottle cap liners. Each drop immediately spread in a circle 1.5 cm in diameter. About one day in room atmosphere was allowed for evaporation of volatile components and curing of the silicone polymer to a solid discontinuous silicone barrier enveloping the indicator powder particles.

Crude oil test samples contained known concentration of hydrogen sulfide at 1, 2, 3, 5, 8, 12 and 20 ppm. Each crude oil test sample was 100 ml in volume and test containers were 125-ml polypropylene bottles with necks. Screw caps were secured to the necks of the polypropylene bottles, each cap being provided with a plastic Mylar liner having secured thereto lead acetate indicator particles dispersed in the discontinuous solid silicone barrier. The silicone indicator dispersion was deposited on the matte surface of Mylar sheet rather than directly on the interior of the closure caps because the Mylar sheet provided better adhesion for the silicone barrier than the plastic surface of the caps.

The polypropylene test containers were then inverted and gently swirled for 5 minutes. The containers were then turned right side up and the caps were removed. Residual crude oil was removed from the surface of the cap liner with a gentle stream of hexane and hydrogen sulfide concentrations in the samples were correlated with the indicator colors on the standard.

The colors of the silicone-indicator circles ranged from barely detectable at 1 ppm to dark brown at 20 ppm hydrogen sulfide. Visual distinctions of ±1 ppm at 5 ppm or less of hydrogen sulfide could be made and distinctions of ±2–3 ppm at concentrations of 8–16 ppm of hydrogen sulfide were possible.

EXAMPLE 3

This example demonstrates the use of a mixture of copper sulfate (anhydrous $CuSo_4$) and copper thiocyanate (CuSCN) as hydrogen sulfide calorimetric indicators. The combination of indicators yields a somewhat wider range of intensity of colors than either alone.

Twenty milligrams of powdered anhydrous copper sulfate and 15 mg of powdered copper thiocyanate were thoroughly dispersed in 0.2 ml methyl ethyl ketone and 1.2 ml of 20% fluorosilicone liquid polymer solution to form a thin dispersion of the indicator particles in the silicone solution. The indicators were sufficiently powdered to pass a screen with 44 micron openings. The polymer solution was Dow Corning 94-003 liquid silicone polymer diluted with an equal volume of hexane and centrifuged to remove silica coloring matter. Portions of the dispersion in 0.12 ml amounts were dispersed on the matte surface of a Mylar sheet and each portion of the dispersion spread evenly over a square 4 cm in area. After a day in room atmosphere, the volatile components of the dispersion had evaporated and the silicone polymer cured to a discontinuous barrier about 50 microns in thickness. The supporting Mylar sheet was cut into indicidual squares each bearing a barrier layer with embedded indicator.

Seawater test samples containing 6% of a fire-fighring foam (3M FC-206 CF) and known concentrations of hydrogen sulfide were dispensed in 20 ml amounts in 25-ml glass vials. The vial openings were immediately covered with Mylar squares each carrying the silicone film containing the indicator particles dispersed therein, with the silicone barrier containing embedded indicator particles facing the test sample in the vial. The Mylar sheet was pressed down against the vial opening with a rubber pad and gently shaken in an inverted position for 5 minutes.

Examination against a white background of the silicone films having dispersed therein the mixed calorimetric indicators showed that while there was a barely detectable color change at 1 ppm hydrogen sulfide, a gray-green color was easily visible at 2 ppm hydrogen sulfide and the intensity of the color increased progressively with 4, 8, 16 and 32 ppm hydrogen sulfide in the test sample.

Many modifications and variations of the present invention are possible in light of the above descriptions. It is, therefore, to be understood that within the scope of the appended claims, the invention may be practiced otherwise than as specifically disclosed.

What is claimed is:

1. A kit for analyzing the concentration of hydrogen sulfide in a liquid test sample, said kit comprising a test container for receiving and holding a liquid test sample containing hydrogen sulfide, said container having an opening therein, a removable cap provided over the container opening, said cap having on its inner surface indicator particles subject to degradation by the test sample, and a silicone polymer barrier disposed over said indicator, said silicone polymer barrier being permeable to hydrogen sulfide but impermeable to said liquid sample.

2. The kit of claim 1 wherein average particle size of said indicator particles less than 100 microns in size.

3. The kit of claim 2 wherein said silicone barrier is a continuous film and said indicator particles comprise a separate layer, said film being permeable to hydrogen sulfide but substantially impermeable to aqueous and hydrocarbon liquids.

4. The kit of claim 2 wherein the silicone barrier is a layer of silicone having said indicator particles disposed and embedded therein.

5. The kit of claim 2 wherein said particulate indicator produces a calorimetric response when it is contacted by hydrogen sulfide, the intensity of said calorimetric response being proportional to the concentration of hydrogen sulfide in the liquid sample, and wherein the kit includes the test sample selected from the group consisting of aqueous solutions, hydrocarbon liquids, and mixtures thereof.

6. The kit of claim 5 wherein said liquid hydrocarbon is crude oil and wherein said silicone barrier is a cured silicone polymer and in the solid state.

7. The kit of claim 6 wherein said silicone barrier has a thickness in the range of about 20–200 microns.

8. The kit of claim 7 wherein said silicone barrier is selected from the group consisting of cross-linked dimethyl silicone, cross-linked diethyl silicone, cross-linked fluorosilicone, cross-linked methylphenyl silicone, cross-linked ethylphenyl silicone, cross-linked diphenyl silicone, and mixtures thereof.

9. The kit of claim 6 wherein said silicone barrier is cross-linked polysiloxane.

10. The kit of claim 9 including an external standard for determining the amount of hydrogen sulfide in said test sample.

11. The kit of claim 5 wherein said indicator is selected from the group consisting of lead acetate, copper sulfate, copper thiocyanate, silver nitrate, and mixtures thereof.

* * * * *